(12) United States Patent
Linington et al.

(10) Patent No.: US 9,596,855 B2
(45) Date of Patent: Mar. 21, 2017

(54) SMALL MOLECULE INHIBITORS OF BIOFILM FORMATION AND THE NOVEL USE OF PREVIOUSLY IDENTIFIED COMPOUNDS FOR INHIBITION OF BIOFILM FORMATION AND APPLICATIONS FOR DRUG THERAPY AND MEDICAL DEVICE COATING

(71) Applicants: Roger Gareth Linington, Burnaby (CA); Havva Fitnat Gurcan, Santa Cruz, CA (US); Kelly Corbus Peach, Santa Cruz, CA (US); Andrew Cheng, Santa Cruz, CA (US)

(72) Inventors: Roger Gareth Linington, Burnaby (CA); Havva Fitnat Gurcan, Santa Cruz, CA (US); Kelly Corbus Peach, Santa Cruz, CA (US); Andrew Cheng, Santa Cruz, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/768,468

(22) PCT Filed: Feb. 19, 2014

(86) PCT No.: PCT/US2014/017222
§ 371 (c)(1),
(2) Date: Aug. 18, 2015

(87) PCT Pub. No.: WO2014/130587
PCT Pub. Date: Aug. 28, 2014

(65) Prior Publication Data
US 2016/0000079 A1    Jan. 7, 2016

Related U.S. Application Data

(60) Provisional application No. 61/766,558, filed on Feb. 19, 2013.

(51) Int. Cl.
| | |
|---|---|
| A61K 31/535 | (2006.01) |
| A01N 43/84 | (2006.01) |
| A61K 31/538 | (2006.01) |
| A61K 31/541 | (2006.01) |
| A61L 31/08 | (2006.01) |
| A61L 31/16 | (2006.01) |
| C07D 265/36 | (2006.01) |
| C07D 417/06 | (2006.01) |

(52) U.S. Cl.
CPC ............ *A01N 43/84* (2013.01); *A61K 31/538* (2013.01); *A61K 31/541* (2013.01); *A61L 31/08* (2013.01); *A61L 31/16* (2013.01); *C07D 265/36* (2013.01); *C07D 417/06* (2013.01); *A61L 2300/406* (2013.01)

(58) Field of Classification Search
None
See application file for complete search history.

*Primary Examiner* — Jeffrey H Murray
(74) *Attorney, Agent, or Firm* — Adam Warwick Bell; Matthew Rupert Kaser

(57) ABSTRACT

Small molecule compound having a fused heterocyclic ring structure that are substituted derivatives of the Auromomycin Chromophore having the general formula:

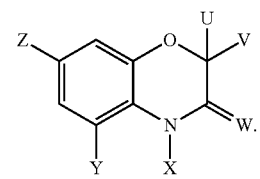

U and V = H, OH, Me, Et, iPr, methylene
W = O, S
X = H, Me, Benzyl
Y = $CO_2Me$, $CO_2H$, $CH_2OH$
$CH_2NH_2$, $CH_2NMe_2$, H
$CH_2OP(O)(ONa)_2$
Z = OMe, OH, H, OAc, $OP(O)(ONa)_2$
$OCH_2C_6H_4OMe$, $OCH_2C_6H_4NO_2$
$OCH_2C_6H_4CF_3$

9 Claims, 1 Drawing Sheet

SMALL MOLECULE INHIBITORS OF BIOFILM FORMATION AND THE NOVEL USE OF PREVIOUSLY IDENTIFIED COMPOUNDS FOR INHIBITION OF BIOFILM FORMATION AND APPLICATIONS FOR DRUG THERAPY AND MEDICAL DEVICE COATING

RELATION TO OTHER APPLICATIONS

This application claims the benefit of and priority to U.S. provisional application No. 61/766,558 filed 19 Feb. 2013, titled "Novel small molecule inhibitors of biofilm formation and the novel use of previously identified compounds for inhibition of biofilm formation and applications for drug therapy and medical device coating" which is hereby incorporated by reference for all purposes.

GOVERNMENT SPONSORSHIP

This work was sponsored by US government grant NIH (NIAID) 1R21AI098836-01, the Government has certain rights in the invention.

FIELD OF THE INVENTION

Small molecule therapeutics for inhibition of biofilm formation.

BACKGROUND

Inhibition of biofilm formation can play a very important role in contributing to pathogenicity. Bacteria in the biofilm state have been shown to be 10-10,000-fold less susceptible to antibiotic treatment. Estimations made by the Centers for Disease Control (CDC) and the National Institutes of Health (NIH) attribute 65% to 80% of human infections as biofilm mediated. Consequently, biofilm formation is often responsible for chronic infections due to bacterial persistence despite antibiotic treatment. Considering that the formation of biofilms undermines the utility of existing antibiotics, our research team is interested in the development of new solutions that specifically address biofilm formation. To date, very few compounds have been shown to selectively inhibit biofilm formation in a non-microbicidal manner.

It has been suggested that the development of biofilm inhibitors may restore susceptibility to antibiotics in pathogenic infections, thus renewing the utility of existing therapies, particularly therapies employing antibiotics that show low human toxicity. Treatment strategies employing co-dosing of antibiotics and compounds disrupting biofilm formation may therefore provide a new avenue for combating antibiotic resistance.

Additionally, small molecule biofilm modulators have promising potential for development as coatings for indwelling medical devices. Medical implant devices are a major source of nosocomial infections. Compound coatings of this nature could therefore prevent initial bacterial colonization of these surfaces, and reduce the instances of persistent bacterial infections among inpatient populations.

By discovering new classes of biofilm inhibitor such as the compound described below, and by discovering the novel use of previously described compounds, we shall develop a suite of tools for drug therapy and medical device coating.

BRIEF DESCRIPTION OF THE INVENTION

Biofilm formation is very strongly linked with pathogenesis for many infective organisms. The invention encompasses novel compounds and the novel use a class of previously identified small molecules for the inhibition of biofilm formation.

The small molecule compounds of the invention include purified products and substituted derivatives of the Auromomycin Chromophore derived from a marine organism. The present disclosure is the first instance of the use of such compounds to inhibit biofilm formation.

Examination of a prefractionated library of microbially-derived marine natural products has led to the identification of a new biofilm inhibitor that is structurally unrelated to previously reported inhibitors and is one of the most potent inhibitors reported to date against $V.\ cholerae$. Combination of this compound with sub-MIC (minimum inhibitory concentration) concentrations of a number of clinically relevant antibiotics was shown to improve the biofilm inhibitory efficacy of this new compound compared to monotherapy treatments, and provides evidence for the potential therapeutic benefit of biofilm inhibitors in treating persistent biofilm-mediated infections.

The invention includes compounds (and methods) for the inhibition of biofilm colonization that may be used with and without traditional antibiotics and offers a unique approach to the elimination of persistent biofilm-mediated bacterial infections.

The invention has a number of important applications including medical device coatings to prevent colonization and co-therapies with antibiotics for the treatment and prevention and treatment of various infections, including hospital acquired (nosocomial) infections, such as, for example, $Staphylococcus\ aureus$, $Acinetobacter$ and $Klebsiella$ infections. Other organisms of interest include any pathogenic organism that produces a biofilm, for example $Vibrio\ cholera$.

Medical devices are well known to be susceptible to biofilm colonization and in the present invention may be coated with a composition comprising a compound or the invention. Medical devices may include stents, any implanted device, whether permanent, semi-permanent or temporary, prosthetic devices such as artificial hones such as hip bones, and structural implants such as plates, pins and screws.

In one embodiment the invention includes a method for inhibiting biofilm formation by an organism on a surface the method comprising contacting the organism or the surface with a compound having a fused heterocyclic ring structure. The compound may have the following formula:

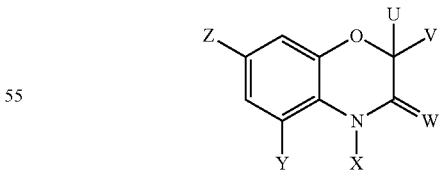

2

U and V = H, OH, Me, Et, iPr, methylene
W = O, S
X = H, Me, Benzyl
Y = CO$_2$Me, CO$_2$H, CH$_2$OH
CH$_2$NH$_2$, CH$_2$NMe$_2$, H
CH$_2$OP(O)(ONa)$_2$
Z = OMe, OH, H, OAc, OP(O)(ONa)$_2$
OCH$_2$C$_6$H$_4$OMe, OCH$_2$C$_6$H$_4$NO$_2$
OCH$_2$C$_6$H$_4$CF$_3$ Or alternatively the compound may have the following formula:

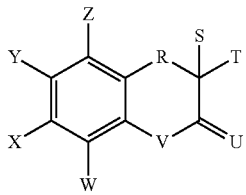

S and T = H, OH, Me, Et, iPr, methylene
U = O, S
V = C, NH, NMe, NBenzyl, O, S
W = $CO_2Me$, $CO_2H$, $CH_2OH$
$CH_2NH_2$, $CH_2NMe_2$, H
$CH_2OP(O)(ONa)_2$
X = H, F
Y = OMe, OH, H, OAc, $OP(O)(ONa)_2$
$OCH_2C_6H_4OMe$, $OCH_2C_6H_4NO_2$
$OCH_2C_6H_4CF_3$
Z = H, F Or in one embodiment the compound may have the following formula:

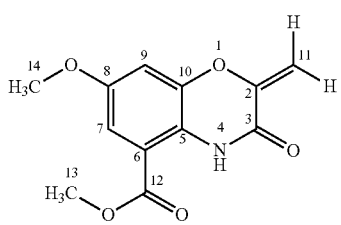

compound 5

In some embodiments the compound exhibits no bactericidal activity and no mammalian cell cytotoxicity. The method may further comprise contacting the organism or the surface with an antibiotic. The antibiotic may be selected from (but is not limited to) beta-lactam antibiotics, cephalosporins, glycopeptides, lipopeptides, macrolides, monobactams, nitrofurnas, oxazolidonones, quinolones, sulphonamides, tetracyclines and sulfur drugs. The surface may be a biological tissue or an inorganic surface such as the surface of a medical device.

Other embodiments include a composition for inhibiting biofilm formation, the composition comprising a heterocyclic compound having the formula above. The composition may further comprise an antibiotic, for example including a beta-lactam antibiotics, cephalosporins, glycopeptides, lipopeptides, macrolides, monobactams, nitrofurnas, oxazolidonones, quinolones, sulphonamides, tetracyclines and sulfur drugs.

DEFINITIONS AND REPRESENTATIONS CONCERNING THE DISCLOSURE

Figure 1A:
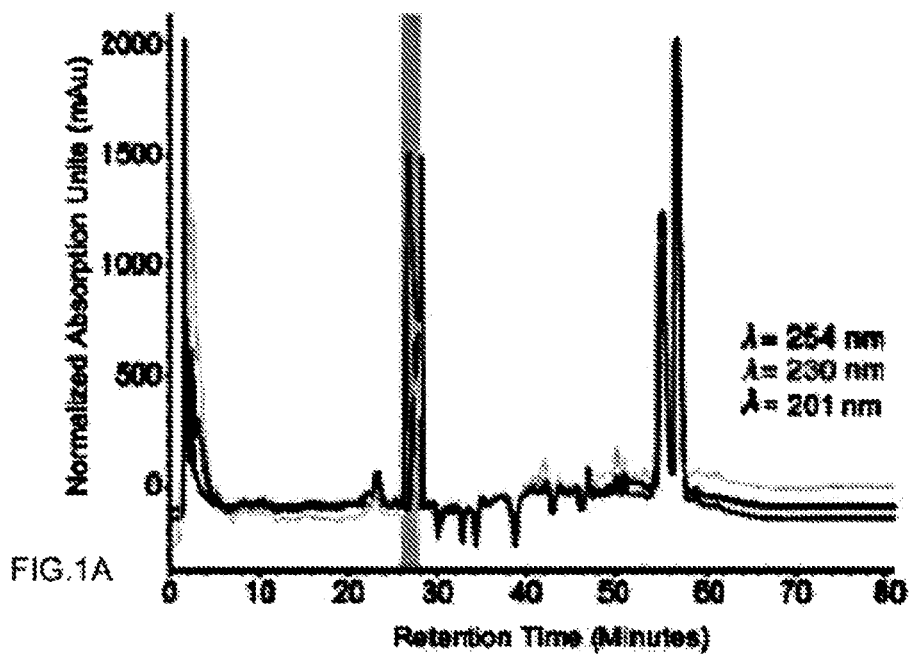
FIG. 1A is a graph of Absorption (mAu) vs. Retention time (mins)

MIC=minimum inhibitory concentration
BIC=biofilm inhibitory concentration in terms of biofilm coverage
When the disclosure refers to "a surface", for example "biofilm formation on a surface" the surface may be any surface and is not limited to a specific surface, but may include a biological surface such as a biological tissue surface or any kind (a mucous membrane, epidermis etc) or such as an experimental synthetic surface such as a polymer surface (such as in a Petri dish) or a synthetic surface coated with organic matter such as a cell culture of protein matrix. The nature of the surface is not an essential part of the invention, but the method of inhibiting biofilm formation is.

Note that although *V. cholera* was used as a standard test organism, the application of the present work is not limited to treatment of disease caused by *V. cholera* buy may be applied to any pathogenic organism that produces a biofilm.

The term "pathogen" in this disclosure is used broadly to mean any organism that is known to cause a pathology by infection of an animal subject. The term "disease" is used to mean any state of an animal that deviates from normal healthy physiology and that is clinically detectable.

The term "binds" or "binding" in connection with the interaction between a one compound or molecule and another compound or molecule, such as a target and a potential binding compound, indicates that the potential binding compound associates with the target to a statistically significant degree as compared to association with proteins generally. Thus, the term "specific binding" refers to binding between two molecules or compounds that is statistically significantly higher than non-specific binding to another molecule. Preferably a binding compound interacts with a specified target with a dissociation constant (k.sub.d) of 1 mM or less, for example 0.1-100 nM. A binding compound can bind with "low affinity", "very low affinity", "extremely low affinity", "moderate affinity", "moderately high affinity", or "high affinity" as described herein. In the context of compounds binding to a target, the term "greater affinity" indicates that the compound binds more tightly than a reference compound, or than the same compound in a reference condition, i.e., with a lower dissociation constant. In particular embodiments, the greater affinity is at least 2, 3, 4, 5, 8, 10, 50, 100, 200, 400, 500, 1000, or 10,000-fold greater affinity. Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. Typically, the specificity is with reference to a limited set of other biomolecules. In particular embodiments, the greater specificity is at least 2, 3, 4, 5, 8, 10, 50, 100, 200, 400, 500, or 1000-fold greater specificity.

The term "derivative" or "derivative compound" or "analogue" refers to a compound having a chemical structure that contains a common core chemical structure as a parent or reference compound, but differs by having at least one structural difference, e.g., by having one or more substituents added and/or removed and/or substituted, and/or by having one or more atoms substituted with different atoms. Unless clearly indicated to the contrary, the term "derivative" does not mean that the derivative is synthesized using the parent compound as a starting material or as an intermediate, although in some cases, the derivative may be synthesized from the parent.

The term "fragment" refers to a part of a larger whole, for example a fragment of a molecule may be any dissociated part of that molecule, regardless of size.

The term "specie" or "group" when used to describe an "R" group in a chemical formula, is used to mean any chemical compound, sub-compound or substituent that may chemically interact with (covalently, ionically or by Van der Waal's forces) another molecule or group such as shown on a chemical formula.

The terms "formulation, "drug formulation or "pharmaceutical formulation," refers to a drug combined with a non-drug such as a carrier material designed not to have a pharmaceutical activity, such as pharmaceutical excipient, filler, or carrier material that may be used to modify or improve the drug release, improve its physical and/or chemical stability, dosage form performance, processing, manufacturing, etc.

When a "terminus" or "terminal group" is discussed as having a substituent, side-chain, group or moiety attached, that substituent, side-chain, group or moiety may equally be present at one or more termini or at side locations along the length of the molecule.

The terms "drug" or "therapeutic agent" mean any substance meant to affect the physiology of a subject. Examples of drugs are described in well known literature references such as the Merck Index and the Physicians Desk Reference.

The term "therapeutically effective amount" means an amount of a therapeutic agent, or a rate of delivery of a therapeutic agent, effective to facilitate a desired therapeutic effect. The precise desired therapeutic effect will vary according to the condition to be treated, the formulation to be administered, and a variety of other factors that are appreciated by those of ordinary skill in the art.

The term "diagnostic agent" means any chemical moiety that may be used for diagnosis or in a diagnostic test. For example, diagnostic agents include imaging agents containing radioisotopes, contrasting agents containing for example iodine, enzymes, fluorescent substances and the like.

The term "treatment" means the application of a process to an individual in order to alter a physiological state, whether or not the process includes a curative element.

Where substitutions are mentioned, sometimes in connection with variable "R" groups as shown in the figures, the substituent groups may be selected from, for example, the following: hydrogen, hydroxyl, carboxylate, alkane, alkene or alkyne groups, substituted or unsubstituted heteroatom, alkyl, alkenyl, alkanoyl, aryl, aroyl, aralkyl, alkylamino cycloalkyl, heterocycloalkyl, heteroaryl, or halogen, azido, fluorophore or polypeptide. In certain embodiments the substituent group may comprise branched or un-branched C1-C18 alkyl, C1-C18 substituted alkyl, C1-C18 alkenyl, C1-C18 acyl, amino, substituted amino, wherein the alkyl, alkenyl or acyl is linear or branched, and optionally substituted with a hydroxyl, an ester and its derivatives, 5 a carboxyl and its derivatives. In a particular embodiment, Any R group may be a lower hydrocarbon substituted with alkoxy, substituted alkoxy, imidate, arylthio, or (substituted aryl)thio. In other embodiments, Any R group may be a lower alkyl selected from methyl, ethyl, propyl, isopropyl, butyl, isobutyl, terabutyl and pentyl. In other embodiments, Any R group may be a lower alkenyl selected from vinyl, substituted vinyl, ethynyl, or substituted ethynyl. In other embodiments, Any R group may be a lower alkanoyl selected from formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, and arachidonyl. In other embodiments, Any R group may be lower aryl selected from phenyl, p-tolyl, pchlorophenyl, p-aminophenyl, p-nitrophenyl, p-anisyl. In yet other embodiments, Any R group may be a lower aroyl selected from benzoyl and naphthoyl. In other embodiments, Any R group may be a lower aralkyl selected from benzyl, benzhydryl, p-chlorobenzyl, m-chlorobenzyl, p-nitrobenzyl, benzyloxybenzyl, or pentaflourobenzyl. In certain other embodiments, Any R group may be a lower alkylamino is selected from monoalkylamino, monoaralkylamino, dialkylamino, diaralkylamino, and benzylamino.

It should be noted that the invention encompasses compounds, methods and treatments wherein compounds of the invention, and their derivatives and analogues, sub-components and fragments derived therefrom, may be employed to treat any disease of any organism, either animal or plant.

In this specification, reference is made to particular features of the invention (including for example components, ingredients, elements, devices, apparatus, systems, groups, ranges, method steps, test results, etc). It is to be understood that the disclosure of the invention in this specification includes all appropriate combinations of such particular features. For example, where a particular feature is disclosed in the context of a particular embodiment or a particular claim, that feature can also be used, to the extent appropriate, in the context of other particular embodiments and claims, and in the invention generally. The embodiments disclosed in this specification are exemplary and do not limit the invention. Other embodiments can be utilized and changes can be made. As used in this specification, the singular forms "a", "an", and "the" include plural reference unless the context clearly dictates otherwise. Thus, for example, a reference to "a part" includes a plurality of such parts, and so forth.

The term "comprises" and grammatical equivalents thereof are used in this specification to mean that, in addition to the features specifically identified, other features are optionally present. Where reference is made in this specification to a method comprising two or more defined steps, the defined steps can be carried out in any order or simultaneously. Where reference is made herein to "first" and "second" features, this is generally done for identification purposes; unless the context requires otherwise, the first and second features can be the same or different, and reference to a first feature does not mean that a second feature is necessarily present (though it may be present).

This specification incorporates by reference all documents referred to herein and all documents filed concurrently with this specification or filed previously in connection with this application, including but not limited to such documents which are open to public inspection with this specification, and including the Appendix and all references disclosed and referred to in the appendix. The entirely of the "definitions" sections of the following applications are hereby incorporated by reference for all purposes: PCT/US10/28071, filed 12 Apr. 2010, and WO2009114325 and US20060281914.

DETAILED DESCRIPTION OF THE INVENTION

In the present study, a 1,248-member prefractionated marine natural product library was evaluated for biofilm inhibitory activity using a recently-developed image-based screening platform. Of the prefractions screened, 7 hits showed non-microcidal biofilm inhibitory activity with normalized $OD_{600}$ values greater than 0.7 and normalized percent biofilm coverage values less than 20% (reported as 0.2). Of these, prefraction 1671D showed the strongest effect on biofilm formation. Prefraction 1671D is a semi-purified mixture that contains mixture of several individual compounds. Prefraction 1671D was therefore subjected to one-compound-one-well 'peak library' fractionation using the inventors' standard protocol that automatically separates the constituents of prefractions of interest based on HPLC retention times, and connects specific constituents to observed biological activities through secondary screening.

Screening of the resulting peak library from prefraction 1671D revealed a strong region of biofilm inhibition at minutes 26-28 that corresponded to a single peak in the chromatogram (see Figure). This activity was coupled with a striking biofilm macrocolony phenotype, providing strong justification for purification and full structural characterization of the active constituent. It was from 1671D that "compound 5" was isolated.

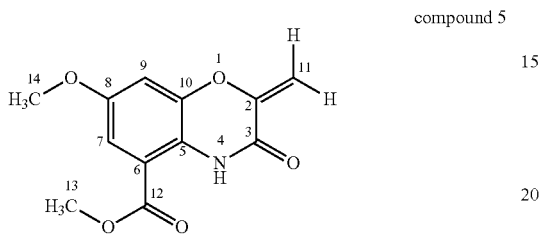

compound 5

Biofilm Inhibitory Activity

In order to determine the biofilm inhibitory activity ($IC_{50}$) of identified compounds, a two-fold dilution series was examined using the inventors' standard imaging platform to afford an $IC_{50}$ of 60.1 µM against *V. cholerae*.

The data from both the epifluorescence and the confocal images indicate that on treatment with compound 5, microcolonies initially become less organized and less tightly packed. This is the first time we have observed this type of biofilm inhibition phenotype in our screening program, and suggests that the biofilm matrix may be being disrupted by a reduction in the production of matrix components involved in controlling biofilm architecture.

In order to further validate the results obtained in the primary screen, we analyzed biofilm formation under static conditions using chambered cover glasses in 1 mL growth medium.

Results revealed that compound 5 had no bactericidal activity against any of the tested strains. Additionally, compound 5 showed no mammalian cell cytotoxicity against HeLa cells, up to the highest tested concentration (250 µM), indicating that compound 5 possesses selective activity for biofilm inhibition without directly impacting either bacterial or host cell survival.

There are very few examples of agents capable of causing inhibition of biofilm formation in *V. cholerae*. Compound 5 is one of only a small number of biofilm inhibitors with activity against *V. cholerae* and is the first example of an inhibitor possessing this fused heterocyclic ring system.

Initial Development of Lead Compound 5

First Generation Approach

Having identified lead compound 5 as a biofilm inhibitor, subsequent work has focused upon the generation of a library of synthetic analogues that surpass the activity of the initial target. The first generation molecules have the generic description as depicted in compound 2 and will have six molecular entities examined to determine their necessity in the biological activity of structure 5 (FIG. 1).

Note that compounds 13 and 30, two carboxylic acid derivatives of compound 5 have been previously synthesized (see *Tetrahedron Letters* 1986, 27, 1351-1354) and as such are not new chemical entities (FIG. 3). The other compounds and substituted derivatives are believed to be entirely novel chemical entities.

Despite their previous identification, however, neither compound 13 or 30 has been previously used as, or formulated for, or reported as a biofilm inhibitor, with the only biological data present in the literature being concerned with the two entities ability to act as DNA cleaving reagents (see above referenced paper for further details).

Figure 1B:
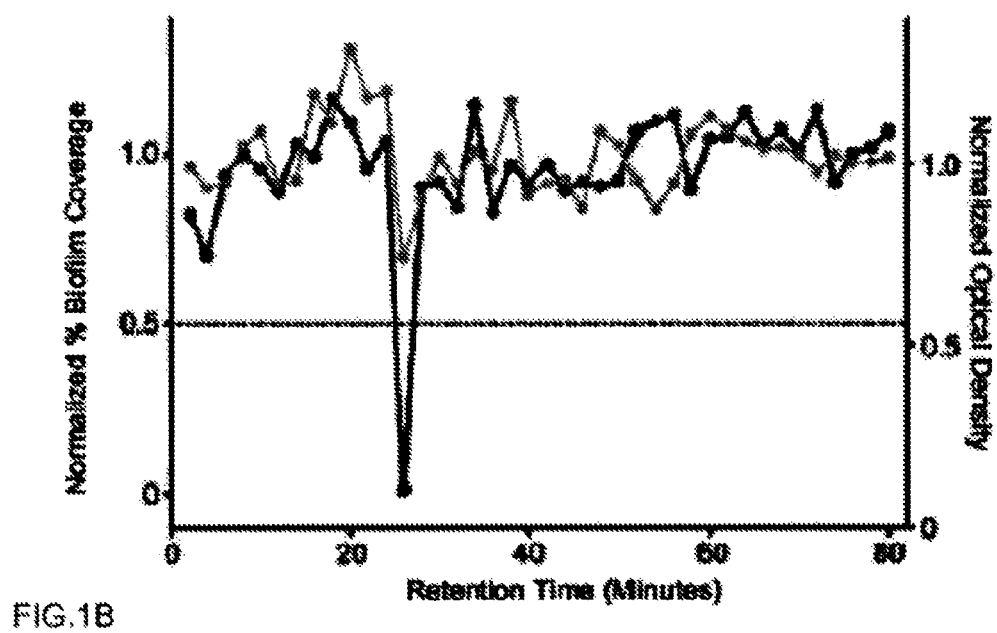
FIG. 1B is a graph of Normalized % biofilm coverage and Normalized Optical Density vs. Retention time (mins)

Figure 1: A generic representation of the first generation analogues of lead compound

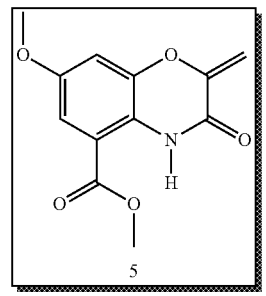

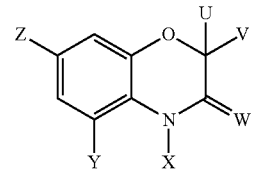

U and V = H, OH, Me, Et, iPr, methylene
W = O, S
X = H, Me, Benzyl
Y = $CO_2Me$, $CO_2H$, $CH_2OH$
$CH_2NH_2$, $CH_2NMe_2$, H
$CH_2OP(O)(ONa)_2$
Z = OMe, OH, H, OAc, OP(O)(ONa)$_2$
$OCH_2C_6H_4OMe$, $OCH_2C_6H_4NO_2$
$OCH_2C_6H_4CF_3$ Figure 2: A generic representation of the first generation analogues with functionalization at the U, V, W and X positions.

Functionalization of the U and V positions

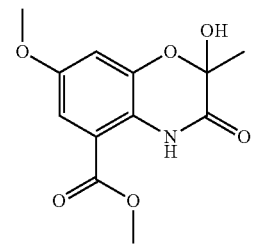

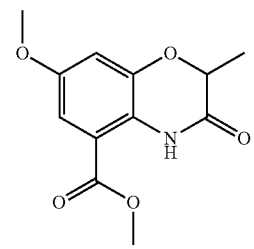

9
-continued
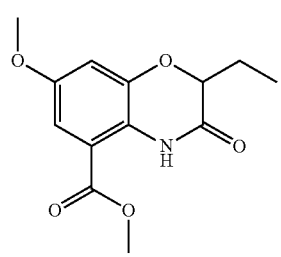
1
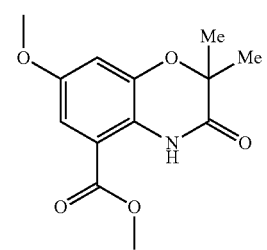
32
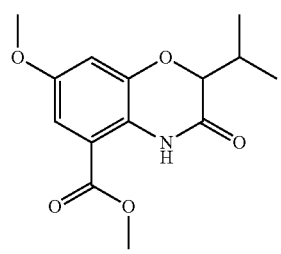
7
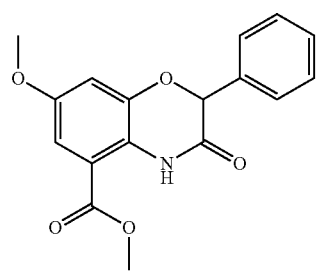
8
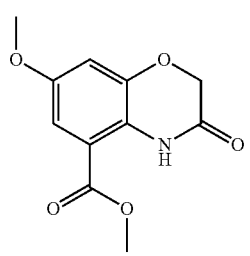
9
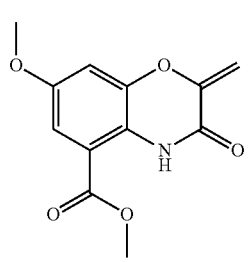
Functionalization of the W position
10
-continued
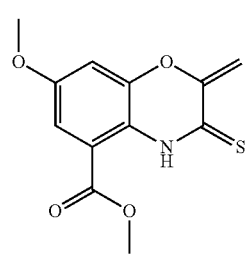
10
Functionalization of the X position
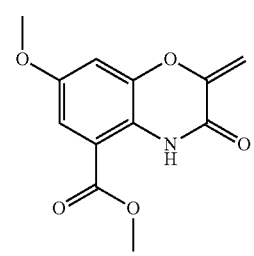
5
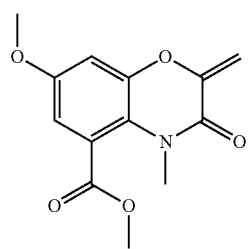
11
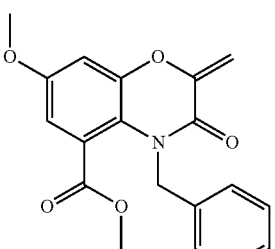
12
Figure 3: A generic representation of the first generation analogues with functionalisation at the Y and Z positions.
Functionalization of the Y position
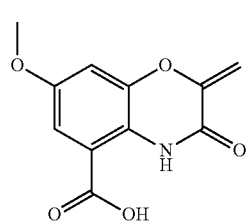
13

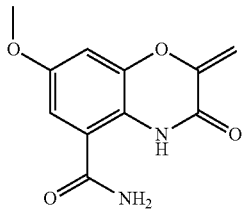
14
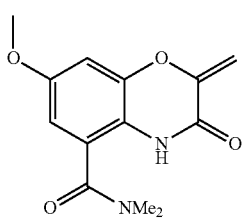
15
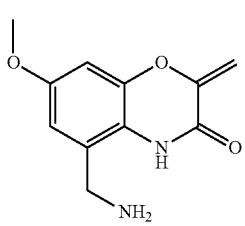
16
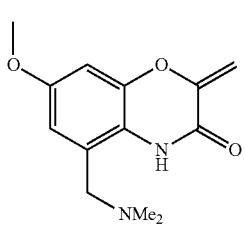
17
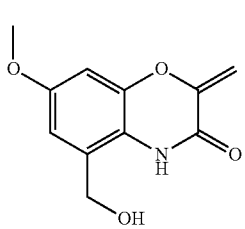
18
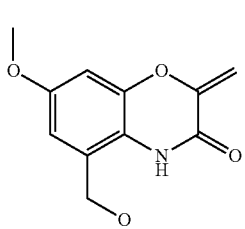
19
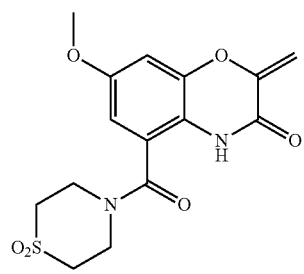
20
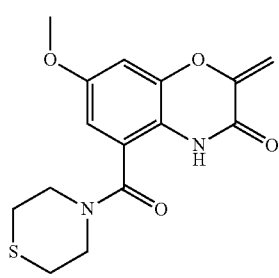
21
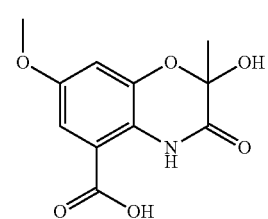
30
Functionalization of the Z position
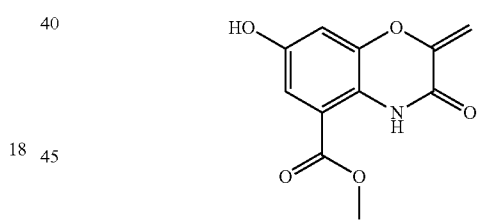
22
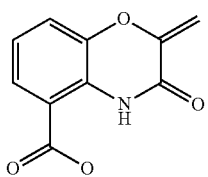
23
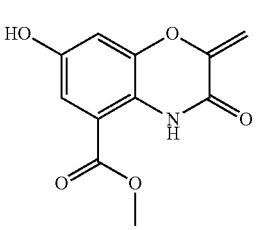
24

-continued

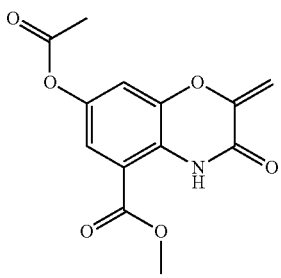
25

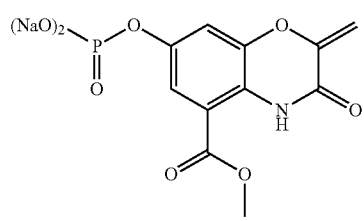
26

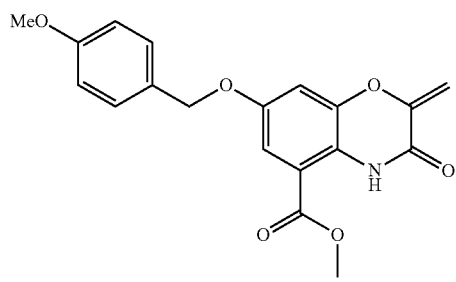
27

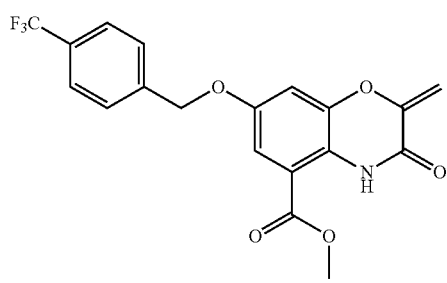
28

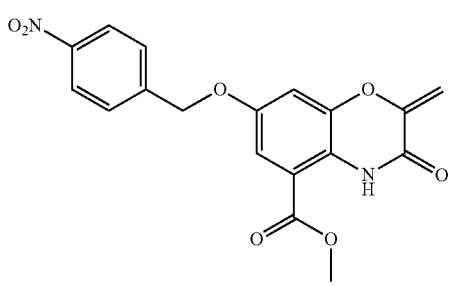
29

Second Generation Strategy

With some first generation analogues of compound 5 proving to be superior improved candidates for pharmaceutical use, a second generation library of molecules is synthesized.

A generic molecule 31 is depicted below in which the possible moieties for each functional site are listed. The purpose of the second generation library is to further improve both the activity and pharmaceutical efficacy of the lead compound in question. The susceptibility for aromatic hydrogen atoms to undergo oxidation warrants the second generation compound to incorporate the analogous fluorine units as to prevent such a process from occurring.

Figure 4: A representation of the second generation substrates that could be expected to be synthesized. The compounds will contain one or more of the functionalities as depicted above.

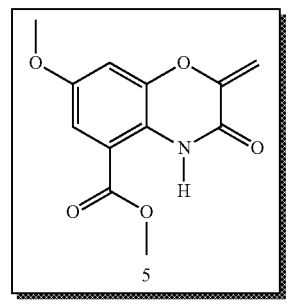
5

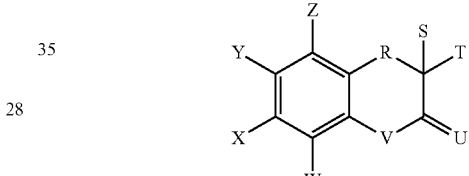
31

S and T = H, OH, Me, Et, iPr, methylene
U = O, S
V = C, NH, NMe, NBenzyl, O, S
W = $CO_2Me$, $CO_2H$, $CH_2OH$
$CH_2NH_2$, $CH_2NMe_2$, H
$CH_2OP(O)(ONa)_2$
X = H, F
Y = OMe, OH, H, OAc, $OP(O)(ONa)_2$
$OCH_2C_6H_4OMe$, $OCH_2C_6H_4NO_2$
$OCH_2C_6H_4CF_3$
Z = H, F Co-Dosing of Biofilm Inhibitors with Sub-Mics of Antibiotics It is well-documented that sub-MIC (minimum inhibitory concentration) doses of antibiotics are capable of inducing bacterial biofilm formation in vitro. In 2005, a study reported in Nature illustrated the biofilm-inducing properties of sub-MIC concentrations of tobramycin, and the following years resulted in dozens of additional publications reporting similar results. To date, tetracycline has been shown to induce biofilm formation in five different bacterial species, and rifamycin in three different bacterial species. These studies raise concerns that therapeutic treatments of infections where prescribed antibiotics are not administered at sufficiently high doses may be contributing to the severity and persistence of infections by inducing biofilm formation. This is of concern for treatment of bacterial infections, since bacterial biofilms are inherently less responsive to antibiotic treatment. Thus, it has been suggested that the development of cotherapeutic agents to suppress biofilm induction could serve as a valuable solution to this problem by restoring antibiotic susceptibility.

Three commercially available antibiotics, tetracycline, ceftazidime, and ciprofloxacin, were chosen for evaluation using this strategy due to their orthogonal bacterial targets and their utility as therapeutics against *V. cholerae* infections. Dilution series for each antibiotic were evaluated using our image-based screen in order to determine both sub-MIC and sub-BIC (biofilm inhibitory concentration in terms of biofilm coverage) concentrations. A dilution series of compound 5 was then co-treated with a single fixed concentration of each antibiotic (a concentration qualifying as both sub-MIC and sub-BIC). This allowed us to evaluate whether the biofilm inhibition efficacy of compound 5 was affected by the addition of sub-MIC and sub-BIC levels of antibiotics.

These results indicate that the addition of low concentrations of antibiotics significantly enhance the biofilm inhibitory activity of compound 5. Addition of sub-BIC quantities of tetracycline improved biofilm clearance by halving the concentration of compound 5 required to cause a 50% decrease in biofilm coverage. Sub-BIC concentrations of ceftazidime and ciprofloxacin were also found to improve the biofilm-clearing efficacy of compound 5, suggesting that this strategy is broadly applicable to antibiotics with different modes of action.

Any type of antibiotic may be employed with the invention, including, but not limited to penicillins and other beta-lactam antibiotics, penicillin combinations, cephalosporins, glycopeptides, lipopeptides, macrolides, monobactams, nitrofurnas, oxazolidonones, quinolones, sulphonamides, tetracyclines, sulfur drugs, and, for example, tobramycin rifamycin, ceftazidime, and ciprofloxacin.

CONCLUSION

This study reports the discovery of a new structural class of biofilm inhibitors, discovered through the application of an image-based, high-throughput screening platform to our in-house prefractionated marine natural products library. Using this target-independent phenotypic screening platform in concert with standard antibiotic and cytotoxicity assays we have demonstrated that this compound is a selective, non-bactericidal inhibitor of *V. cholerae* biofilms, and possesses a unique phenotype, causing diffuse microcolony formation. By shifting the focus of therapeutic discovery from antibiotic development to a more subtle inhibition of biofilm colonization we have identified a compound with potential to restore the efficacy of traditional antibiotics that is orthogonal to existing therapeutic options, and offers a unique approach to the elimination of persistent biofilm-mediated bacterial infections.

Various embodiments and supporting information are disclosed in the APPENDIX.

The invention claimed is:
1. A method for inhibiting biofilm formation by an organism on a surface, the method comprising contacting the organism or the surface with a compound having a fused heterocyclic ring structure wherein the compound has the following formula:

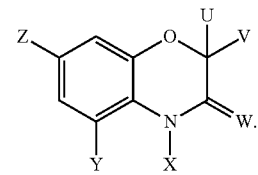

U and V = H, OH, Me, Et, iPr, methylene
W = O, S
X = H, Me, Benzyl
Y = CO$_2$Me, CO$_2$H, CH$_2$OH
CH$_2$NH$_2$, CH$_2$NMe$_2$, H
CH$_2$OP(O)(ONa)$_2$
Z = OMe, OH, H, OAc, OP(O)(ONa)$_2$
OCH$_2$C$_6$H$_4$OMe, OCH$_2$C$_6$H$_4$NO$_2$
OCH$_2$C$_6$H$_4$CF$_3$ 2. The method of claim 1 wherein the compound has the following formula:

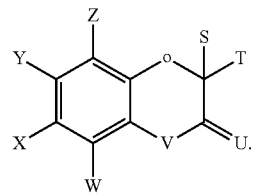

S and T = H, OH, Me, Et, iPr, methylene
U = O, S
V = C, NH, NMe, NBenzyl, O, S
W = CO$_2$Me, CO$_2$H, CH$_2$OH
CH$_2$NH$_2$, CH$_2$NMe$_2$, H
CH$_2$OP(O)(ONa)$_2$
X = H, F
Y = OMe, OH, H, OAc, OP(O)(ONa)$_2$
OCH$_2$C$_6$H$_4$OMe, OCH$_2$C$_6$H$_4$NO$_2$
OCH$_2$C$_6$H$_4$CF$_3$
Z = H, F 3. The method of claim 1 wherein the compound has the following formula:

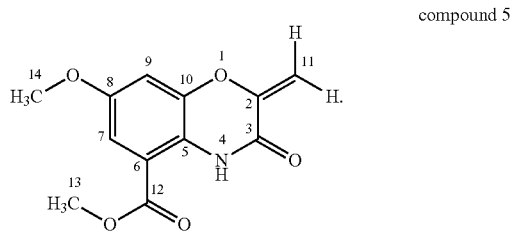

compound 5

4. The method of claim 1 wherein the compound exhibits no bactericidal activity and no mammalian cell cytotoxicity.
5. The method of claim 1 further comprising contacting the organism or the surface with an antibiotic.
6. The method of claim 5 wherein the antibiotic is selected from beta-lactam antibiotics, cephalosporins, glycopeptides, lipopeptides, macrolides, monobactams, nitrofurnas, oxazolidonones, quinolones, sulphonamides, tetracyclines and sulfur drugs.
7. The method of claim 1 wherein the surface is a biological tissue.
8. The method of claim 1 wherein the surface is an inorganic surface.
9. The method of claim 8 wherein the surface is the surface of a medical device.

* * * * *